United States Patent [19]

King

[11] Patent Number: 5,229,372
[45] Date of Patent: Jul. 20, 1993

[54] CONTROL OF POULTRY DACTYLARIOSIS

[75] Inventor: Bruce D. King, Troy, Ill.
[73] Assignee: Du Coa L.P., Highland, Ill.
[21] Appl. No.: 938,328
[22] Filed: Aug. 31, 1992

Related U.S. Application Data

[63] Continuation of Ser. No. 729,376, Jul. 12, 1991, abandoned.

[51] Int. Cl.$^5$ ............................................. A61K 31/70
[52] U.S. Cl. ........................................................ 514/31
[58] Field of Search ............................................ 514/31

[56] References Cited

U.S. PATENT DOCUMENTS

| | | | |
|---|---|---|---|
| 3,343,968 | 9/1967 | Huhtanen | 424/119 |
| 4,536,494 | 8/1985 | Carter | 514/31 |
| 4,600,706 | 7/1986 | Carter | 514/31 |

OTHER PUBLICATIONS

F. T. W. Jordan, Poultry Diseases, Bailliere Tindall, 3rd Ed., pp. 216-217.
Florey, Analytical Profiles of Drug Substances, vol. 10, 1981, p. 517.
W. P. Raab, Natamycin (Pimaricin), Georg. Thieme Publishers Stuttgart, pp. 18-19.

Primary Examiner—Frederick E. Waddell
Assistant Examiner—K. Weddington
Attorney, Agent, or Firm—Robert J. Reichert

[57] ABSTRACT

Post-hatch diseases in poultry caused by Dactylaria gallopava are prevented and treated by exposing the poultry environment to an effective quantity of natamycin.

10 Claims, No Drawings

CONTROL OF POULTRY DACTYLARIOSIS

This application is a continuation of application Ser. No. 07/729,376, filed Jul. 12, 1991, now abandoned.

FIELD OF THE INVENTION

The present invention relates to a method for preventing and controlling post-hatch dactylariosis in poultry by applying an effective amount of natamycin to the litter and/or respiratory system of the poultry.

BACKGROUND OF THE INVENTION

Dactylariosis is a common poultry fungal disease that usually attacks the respiratory system, although other sites may be involved. Dactylariosis is typically caused by *Dactylaria gallopava* mold, which is a member of the fungus family. *Dactylariosis gallopava* will proliferate in aerobic environments, particularly with a high humidity and a temperature over about 25° C. Moldy litter, grain and feed, dust and unclean hatching equipment have been associated with dactylariosis outbreaks.

Inhalation of the spores of *Dactylaria gallopava* appears to be the primary route of exposure, with young chicks and poults being the most susceptible to an infection.

Post-hatch dactylariosis can also be egg borne, with the mold growing inside the egg. Chicks hatching from such eggs have a high disease risk. Further, outbreaks of dactylariosis are common in young birds, usually occurring within 1–3 weeks of age. A mortality rate of 10–50% is usual in an outbreak of dactylariosis.

Symptoms of the dactylariosis disease are: stunting of growth, gasping, rapid respiration rate, lethargy and increased thirst. The affected poultry may also exhibit leg paralysis, incoordination, torticolis and encephalitis. Encephalitis typically causes lesions in the cerebal cerebellar or optic lobes regions of the poultry. The presence of one or more of these symptoms is not conclusive of a dactylariosis infection. Clinical identification of the mold in affected birds is the only positive diagnosis.

As discussed by F. T. W. Jordan in "Poultry Diseases", Bailliere Tindall, 3rd Edition, pages 216–217, at present there is no feasible treatment for dactylariosis. Affected and infected birds normally are destroyed and the environment must be cleaned rigorously and disinfected.

In the past eggs have been disinfected with a number of agents including natamycin (U.S. Pat. No. 3,343,968). Treating eggs with nataymcin is helpful but does not control dactylariosis attributable to post-hatching environmental conditions.

Natamycin is a member of the polyene family of antimycotics. The compound natamycin is a tetraene with a molecular weight of about 666, an empirical formula corresponding generally to $C_{33}H_{47}NO_{13}$, and contains a glycosidically-linked carbohydrate moiety, mycosamine. It has an isoelectric point of pH 6.5. The structure of natamycin typically exists in two configurations: the enol-structure and the keto-structure.

Natamycin is known as an antibiotic in humans which is discussed in Florey, "Analytical Profiles of Drug Substances", Vol. 10, 1981. As reported in "Pharmacology", Natamycin (Pimaricin) by Wolfgang P. Raab, 1972, Georg Thieme Publishers, Stuttgart, pages 18 and 19, yeasts and molds which infect humans usually exhibit susceptibility to natamycin. The disclosure of each of the above publications is hereby incorporated by reference.

It is an object of the present invention to use natamycin for controlling and preventing diseases in poultry associated with the *Dactylaria gallopava* mold. The environmental characteristics of the sites on humans and poultry, which may be infected by *Dactylaria gallopava*, are diverse and, accordingly, the effectiveness of natamycin against a poultry infection of *Dactylaria gallopava* was a surprising discovery. The surprising effectiveness of natamycin against diseases in poultry associated with *Dactylaria gallopava* is emphasized when considering the anatomical, metabolic, etc. differences between humans and poultry.

It is a specific object of the present invention to prevent and control diseases caused by an infection of *Dactylaria gallopava* by including natamycin in the litter and/or atmosphere of the poultry husbandry environment.

Although particular emphasis is placed upon controlling and preventing diseases associated the particular strain of *Dactylaria gallopava* which affects poultry, other avians (e.g., ducks, turkeys, pheasants, etc.) may be effectively treated in accordance with the present invention. In addition the invention may be used to control and prevent diseases caused by molds which are related to *Dactylaria gallopava*.

SUMMARY OF THE INVENTION

The present invention is a method for preventing and controlling diseases associated with Dactylaria gallopava (hereinafter referred to as "Dactylaria"). A disease in poultry caused by an infection of Dactylaria, known as dactylariosis, can be prevented and controlled by exposing the poultry (e.g., respiratory tract) and/or their environment to an effective amount of natamycin.

In one aspect of the invention, dactylariosis caused an infection of Dactylaria may be controlled and prevented by contacting the poultry's litter with natamycin.

In another aspect of the invention, dactylariosis caused by an infection of Dactylaria may be prevented and controlled by exposing the respiratory system of the poultry to an effective amount of natamycin.

Moreover, early treatment with natamycin can prevent a mold infection. Therefore, it is desirable to treat the litter and/or newly hatched chicks or poults (e.g., within three weeks of hatching), with natamycin which may be followed by periodic treatment throughout the life of the poultry.

DETAILED DESCRIPTION OF THE INVENTION

The method of the present invention relates broadly to the prevention and control of diseases associated with an undesired mold known as *Dactylaria gallopava* (hereinafter referred to as "Dactylaria"). The undesired mold may infect or invade the bodies of the poultry to cause a disease known as dactylariosis which is contagious and normally fatal. The invention achieves prevention and control of diseases associated with Dactylaria by controlling, if not eliminating, growth of the undesired mold.

The undesired mold typically grows within and upon the litter that is used by the poultry. In turn, the Dactylaria may infect the respiratory system of the poultry due to the close proximity of the poultry to the litter. For example, the Dactylaria within the litter can produce spores which may become air-borne and carried to the nearby poultry. The spores may be inhaled by the poultry and infect the respiratory system of the poultry to cause dactylariosis.

The method of the invention is achieved by exposing the litter, and/or the poultry to an effective dosage of natamycin. An effective dosage of natamycin typically ranges from about 1.0 part per million (ppm) through about 70 ppm and normally about 5–30 ppm of the environment being treated. However, the exact dosage which is sufficient to be effective against the Dactylaria is dependent upon the specific environment which contains the undesired mold. In accordance with the invention, the term environment is intended to refer to the litter, infection site of the poultry, etc., which may be adversely affected by Dactylaria. If the environment is favorable for the metabolic activities of the mold, a relatively large dosage of natamycin may be required to be effective against the mold(e.g., 20–30 ppm of natamycin). An environment which is warm, possesses a neutral pH, contains oxygen, includes a substrate (e.g., a metabolizable food source), which enhances mold growth, etc., would require a relatively large dosage of natamycin to be effective against the undesired mold. The amount of natamycin which is necessary to prevent growth and a possible infection of the undesired mold is less than the amount of natamycin which is necessary to treat an existing mold infection. Therefore, it is advantageous to treat the environment in accordance with the invention while the chicks or poults are in the early stages of their development (e.g., treat the chicks immediately after hatching to prevent an infection of the undesired mold).

Moreover, although it is preferred to practice the invention by using natamycin, pharmaceutically acceptable derivatives of natamycin (e.g., calcium and sodium salts, and esters of natamycin), which are effective to control and prevent exposure of the poultry to Dactylaria, may be used in the invention alone or in conjunction with natamycin. The preferred morphology of the natamycin is crystalline; however, any morphological state is acceptable in practice of the invention which is effective against Dactylaria. Further, the natamycin used in the invention may be present in one or more hydrate forms (e.g., mono-, di and tri-hydrates). The tri-hydrate form is advantageous for some applications due to its stability. In some cases it may be desirable to increase the effectiveness of the natamycin by comminuting or grinding the natamycin to increase the surface area of the natamycin.

In one embodiment of the invention, the litter which is used by the poultry may be treated with natamycin. A suitable litter comprises at least one member of the following group: clay, hard wood planks, wood shavings, etc. The natamycin (e.g., in a crystalline form) may be applied directly to the litter in any expedient manner. For example, the natamycin may be suspended within a non-toxic carrier liquid and sprayed upon the litter. Should a non-toxic carrier liquid be used to apply the nataymcin to the litter, the carrier liquid should generally not be a solvent for the natamycin. However, certain pharmaceutically acceptable derivatives of natamycin may be soluble within the non-toxic carrier liquid. Suitable non-toxic carrier liquids comprise at least one member of the following group: alcohols such as methanol, water, etc. When an effective amount of natamycin is used to treat the litter, growth (e.g., sporation) of Dactylaria is reduced, if not eliminated, which tends to prevent an Dactylaria infection in the respiratory system of the poultry. For example, in a comparison between two groups of poultry that use a litter contaminated with Dactylaria, one group having litter treated with natamycin and the second group having untreated litter, it would be expected that at least about 15% of the poultry in the second group(untreated liter) will contract dactylariosis within a period of about 14 days.

Moreover, depending upon the concentration of Dactylaria in the litter, it may be desirable to treat the litter with natamycin before and during use by the poultry. Further, in certain situations it may be advantageous to continue to treat the litter with natamycin after the soiled litter has been removed for disposal (e.g., any disposed litter which is stored near the poultry may release spores capable of infecting the respiratory system of the poultry with Dactylaria).

In another embodiment of the invention, the respiratory systems of the poultry may be contacted with natamycin to prevent and/or control a Dactylaria infection. When the nataymcin is applied effectively to the respiratory system, a Dactylaria infection can be prevented and an existing infection can be controlled, if not eliminated. The natamycin may be applied in any suitable manner which introduces an effective amount of natamycin into the respiratory system of the poultry. A convenient and effective manner for applying the natamycin to the poultry comprises introducing an airborne suspension of nataymcin(e.g., an aerosol, a fog, mist, etc.), into a confined area or chamber (e.g., a so-called "spray cabinet") through which the poultry passes. The poultry may be transported towards, passed through and away from the confined area by any acceptable means, such as, for example, a conveyor belt. The poultry, while within the confined area, inhale the air-borne natamycin which contacts directly their respiratory systems. The poultry should remain within the confined area containing natamycin for a period which is sufficient to permit the poultry to inhale a quantity of nataymcin that is effective to prevent and/or control a Dactylaria infection.

The natamycin suspension(e.g., an aerosol, fog, mist, etc.), may be created by first forming a mixture of natamycin within an appropriate carrier fluid. The carrier fluid must be non-toxic and normally not a solvent for the natamycin. An appropriate fluid comprises at least one member of the following group: alcohols such as methanol, water, etc.

The natamycin suspension discussed above may be converted to an aerosol, a fog, mist, etc., by any technique which creates a respirable form of natamycin for the poultry. For example, an aqueous suspension of natamycin may be pumped through a nozzle, which is in communication with the confined area containing the poultry, at a rate which is sufficient to introduce the fluid into the confined area to create a respirable form of natamycin. Generally, a natamycin suspension having relatively fine particles, enhances the penetration of the natamycin into the respiratory system of the poultry which increases the effectiveness of the natamycin against Dactylaria. For example, in a comparison between two groups of poultry that have been exposed to Dactylaria, one group of poultry having been treated by being exposed to a respirable form of natamycin and a second group of poultry which has not been treated, it would be expected that about 20% of the untreated poultry will contract dactylariosis within a period of about 25 days.

Moreover, in certain situations it may be desirable to treat the entire poultry husbandry environment (e.g., to reduce the activity of any air-borne mold spores). For example, the natamycin may be introduced into the ventilation equipment (e.g., the heating/cooling system of the structure which houses the poultry), in a manner which effectively fumigates the poultry husbandry environment to combat an extreme outbreak of Dactylaria.

The ability of the natamycin to prevent and treat an infection of Dactylaria within the poultry is due in part to the unique anatomy and metabolic characteristics of the poultry. For example, the anatomy of a chicken is such that inhalation of natamycin is effective to prevent or control an infection of Dactylaria throughout a significant portion of the poultry's body(e.g., inhalation of natamycin may treat the respiratory system, crop, certain portions of the digestion system, etc., for dactylariosis).

While not wishing to be bound by any theory or explanation, it is believed that natamycin is active or effective against growth of mold, but not against bacteria. One explanation may be that molds (but not bacteria) contain ergosterol in their membranes.

In general the mold will grow, if the environment is appropriate, until contacting the natamycin. The theorized mechanism of natamycin action is a binding of the natamycin molecule and ergosterol present in the cell membrane of the mold. The complexing with ergosterol is substantiated by the neutralizing effects of ergosterol addition on the antifungal activities of natamycin against the *dactylaria gallopava*. A complex between natamycin and the cell membrane of the mold is believed to alter membrane permeability since natamycin is a relatively large molecule which creates an increased surface pressure which may tend to induce a reorientation of the ergosterol present in the membrane, thus altering permeability of the cell and resulting in osmotic shock. This osmotic shock is sufficient to interrupt, if not halt, the metabolic activities of the Dactylaria(e.g., the natamycin may cause irregular mold growth, sporation, etc.)

In certain aspects of the invention, it may be advantageous to use the natamycin in conjunction with other processes and/or substances. For example, the natamycin suspension may be introduced into the spray cabinet along with a vaccine in order to treat a plurality of poultry ailments.

The natamycin which has been added to the litter and/or formed into a suspension typically possesses an acceptable shelf-life. Depending upon the storage conditions, natamycin can be expected to be effective against the undesired mold for several weeks or months. However, to ensure maximum effectiveness of the natamycin, any unused nataymcin suspension or treated litter should be shielded from extended exposure to light (e.g., a natamycin suspension should be stored in the dark prior to introduction into the spray cabinet).

Any natamycin which is consumed (e.g., inhaled) by the poultry is normally not retained by the poultry. As a result, the natamycin is generally not incorporated into the flesh or eggs of the poultry and, accordingly, does not affect human consumption of any treated eggs or poultry. In contrast, poultry which are exposed to the undesired mold may incorporate the mold and/or toxins thereof into their eggs and flesh. Such mold and/or toxins may be harmful to humans which consume the eggs and poultry flesh; making it is desirable to prevent and control any significant exposure of the poultry to the undesired mold. Therefore, the present invention permits enhanced production of eggs and poultry which are not contaminated with mold and anti-mold agents.

Although a few aspects and embodiments of the invention have been described in detail, those skilled in the art will readily appreciate that the present invention embraces many combinations, equivalents and variations other than those exemplified.

What is claimed is:

1. A method for controlling diseases in poultry caused by *Dactylaria gallopava* comprising:
    treating at least one member of the following group consisting of the poultry litter and the respiratory system of the poultry, by exposure to a quantity of natamycin which is sufficient to reduce growth of the *Dactylaria gallopava*.

2. The method of claim 1 wherein said treating comprises exposing the respiratory system of the poultry to an air-borne suspension of natamycin.

3. The method of claim 2 further comprising fumigating the poultry husbandry environment with a suspension of natamycin.

4. The method of claim 2 wherein the suspension comprises an aqueous mist of natamycin.

5. The method of claim 1 wherein said treating comprises spraying natamycin onto the poultry litter.

6. The method of claim 5 wherein soiled litter is sprayed with natamycin.

7. The method of claim 1 wherein the sufficient quantity of natamycin comprises about 1.0 ppm through about 70 ppm based on the environment being treated.

8. The method of claim 1 wherein the poultry comprises a chicken.

9. The method of claim 1 wherein the poultry comprises a turkey.

10. The method of claim 1 further comprising treating poultry which are infected with a mold comprising *Dactylaria gallopava*.

* * * * *